United States Patent
Rieul et al.

(10) Patent No.: US 10,523,863 B2
(45) Date of Patent: Dec. 31, 2019

(54) OPTICAL ACQUISITION DEVICE FOR BIOMETRIC SYSTEMS

(71) Applicant: MORPHO, Issy-les-Moulineaux (FR)

(72) Inventors: Francois Rieul, Issy les Moulineaux (FR); Sylvaine Picard, Issy les Moulineaux (FR)

(73) Assignee: IDEMIA IDENTITY & SECURITY FRANCE, Issy les Moulineaux (FR)

( * ) Notice: Subject to any disclaimer, the term of this patent is extended or adjusted under 35 U.S.C. 154(b) by 625 days.

(21) Appl. No.: 14/737,410

(22) Filed: Jun. 11, 2015

(65) Prior Publication Data
US 2015/0365589 A1 Dec. 17, 2015

(30) Foreign Application Priority Data
Jun. 13, 2014 (FR) ..................... 14 55447

(51) Int. Cl.
*A61B 5/1171* (2016.01)
*H04N 5/225* (2006.01)
*H04N 5/232* (2006.01)

(52) U.S. Cl.
CPC ....... *H04N 5/23219* (2013.01); *A61B 5/1171* (2016.02); *H04N 5/2254* (2013.01); *H04N 5/23212* (2013.01); *G06T 2207/30196* (2013.01)

(58) Field of Classification Search
CPC ............. H04N 5/23219; H04N 5/2254; H04N 5/23212; A61B 3/14; A61B 5/117;
(Continued)

(56) References Cited

U.S. PATENT DOCUMENTS

2008/0165322 A1* 7/2008 Su ............................ A61B 3/12
351/211
2010/0290668 A1 11/2010 Friedman et al.
(Continued)

FOREIGN PATENT DOCUMENTS

EP          1978394       10/2008
WO     WO-2008131201    10/2008

OTHER PUBLICATIONS

Zhou et al, "Coded Aperture Pairs for Depth from Defocus and Defocus Deblurring" International Journal of Computer Vision. vol. 93, Issue 1, pp. 53-72. 2011 (Year: 2011).*

(Continued)

*Primary Examiner* — Farzana Hossain
(74) *Attorney, Agent, or Firm* — Womble Bond Dickinson (US) LLP

(57) ABSTRACT

The invention relates to a device for acquisition of images for a biometric system, which includes an optical assembly and at least one imager for acquisition of an image of an object to be analysed presented in front of the assembly at a non-determined distance from the latter. The assembly includes at least one diaphragm with a coded aperture. The optical assembly allows acquisition by the sensor(s) of an image of the object capable of being exploited to deduce therefrom the searched biometric information, and of an image of the object acquired via the coded aperture of the diaphragm. The device also includes a processing unit to determine the distance of the object to be analysed as a function of the image of the object acquired via the coded aperture of the diaphragm.

10 Claims, 1 Drawing Sheet

Figure 1:
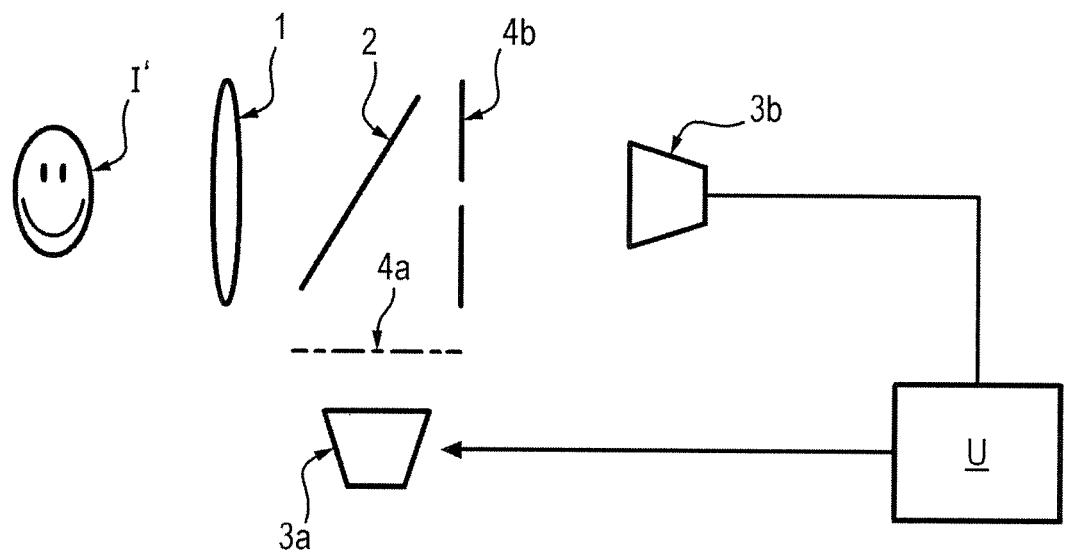

(58) Field of Classification Search
CPC .............. A61B 5/1171; G06K 9/00597; G06T 2207/30196; G06T 7/50
USPC ........................................................ 348/77
See application file for complete search history.

(56) References Cited

U.S. PATENT DOCUMENTS

| | | |
|---|---|---|
| 2011/0032481 A1 | 2/2011 | Uchida et al. |
| 2011/0043666 A1* | 2/2011 | Mitsumoto ........ H04N 5/23209 348/241 |
| 2012/0250159 A1* | 10/2012 | Abramovich ........ G02B 27/123 359/618 |
| 2013/0033578 A1* | 2/2013 | Wajs ..................... G06T 7/0065 348/46 |
| 2013/0194481 A1* | 8/2013 | Golub .................... H04N 9/045 348/336 |
| 2013/0265459 A1* | 10/2013 | Duparre ............. H04N 5/23238 348/218.1 |
| 2014/0361984 A1* | 12/2014 | Kim ........................ G06F 3/013 345/156 |
| 2015/0261299 A1* | 9/2015 | Wajs ....................... G06F 3/011 726/19 |

OTHER PUBLICATIONS

Levin et al. "Image and Depth from a Conventional Camera with a Coded Aperture." ACM Transactions on Graphics. vol. 26, No. 3, pp. 70-1-70-9 (pp. 1-9). Jul. 2007. (Year: 2007).*
French Search Report and Written Opinion, dated Mar. 4, 2015, French Application No. 1455447.

* cited by examiner

OPTICAL ACQUISITION DEVICE FOR BIOMETRIC SYSTEMS

GENERAL TECHNICAL FIELD AND PRIOR ART

The present invention relates to optical acquisition in biometric systems.

It applies particularly advantageously to biometric systems using acquisition of images on the fly ("OTF" or "On The Fly" as per English terminology in general use), for example for identification or authentication by facial recognition, iris acquisition, fingerprint acquisition or venous image acquisition, etc.

Biometric systems conventionally endeavour to know the distance separating the object from the camera, which enables:
- deconvoluting with appropriate deconvolution filter, and therefore canceling blurring;
- activating focusing systems,
- knowing the resolution at which the object is being observed.

The knowledge of this distance is often obtained by projection of a sight and by triangulation between the latter and the sight lines occurring with formation of images. This method is highly efficacious but has the disadvantage of being fairly bulky and disrupting the resulting image by the presence of the sight.

Minimum parallax between the sight and the camera is needed and consequently a certain hindsight.

It is further costly in terms of additional optics and electronics.

It is also already known in optics to use coded apertures on cameras for determining the distance from the object being observed.

Reference could be made for example in this respect to the following articles:

Zhou Et Nayar "Coded Aperture Pairs for Depth from Defocus", 2009-Extended version: International Journal of Computer Vision, May 2011, Volume 93, Issue 1, pp 53-72

Levin et al. "Image and Depth from a Conventional Camera with a Coded Aperture"—ACM transactions on graphics, Vol. 26, no. 3, article 70, July 2007.

The disadvantage of the coded apertures however is that they strongly degrade the quality of the image they produce.

They are consequently generally considered incompatible with highly precise acquisition of images.

GENERAL PRESENTATION OF INVENTION

An aim of the invention is to eliminate the disadvantages of techniques used to date for determining a distance from the object in the case of biometric systems.

More precisely, the invention proposes a solution which is inexpensive and not bulky.

For this purpose, the invention proposes using diaphragms with a coded aperture in biometric systems.

Diaphragm with coded aperture here and throughout the present text means any diaphragm with aperture other than a centred and circular hole, and in particular, but not limited to, any diaphragm aperture consisting of several holes.

More precisely, the invention proposes a device for acquisition of images for a biometric system, comprising an optical assembly and at least one imager for the acquisition of an image of an object to be analysed presented in front of said assembly at a non-determined distance from the latter, characterized in that it comprises at least one diaphragm with coded aperture, the optical assembly being adapted to allow acquisition by the sensor(s):

- on the one hand, of an image of the object capable of being exploited to deduce therefrom the searched biometric information, and
- on the other hand, of an image of the object acquired via the coded aperture of the diaphragm, said device further comprising a processing unit adapted to determine the distance of the object to be analysed as a function of the image of the object acquired via said coded aperture of the diaphragm.

In particular, the optical assembly is advantageously adapted so that the image of the object acquired via the coded aperture serving to determine the distance is acquired in one or more frequency bands separated from the work frequency band(s) used for acquisition of the image carrying the searched biometric information.

Different colours are thus used for the images acquired by the imagers, while the acquisitions of biometric images are generally made by considering only one frequency band.

Advantageously, the optical assembly comprises two colour filters, one transmitting in the work frequency band used for acquisition of the image carrying the searched biometric information, the other transmitting in another frequency band, at least one of these two filters bearing a diaphragm with coded aperture.

In a possible embodiment, the optical assembly comprises at least two diaphragms:
- one diaphragm used for acquisition of the image carrying the searched biometric information, said diaphragm D being fitted with:
  - one aperture (O) at least transparent
    - to work wavelengths ($\lambda w$),
    - to wavelengths ($\lambda d$) for determining the distance
  - a semi-opaque surface being:
    - opaque to work wavelengths ($\lambda w$), and
    - transparent to wavelengths ($\lambda d$) for determining the distance, and
  - said work wavelengths ($\lambda w$) and wavelengths ($\lambda d$) for determining the distance being separate wavelengths,
- a second diaphragm with coded aperture used for acquisition of information for determining the distance, said diaphragm being fitted with:
  - a semi-opaque surface being:
    - opaque to wavelengths ($\lambda d$) for determining the distance, and
    - transparent to work wavelengths ($\lambda w$), and
  - a coded aperture (OC) transparent
    - to work wavelengths ($\lambda w$) and
    - to wavelengths ($\lambda d$) for determining the distance.

According to a preferred embodiment the aperture (O) of the diaphragm is a centred and circular aperture enabling acquisition of an image of high quality of the object in the work wavelengths ($\lambda w$).

According to an alternative embodiment the aperture (O) of the diaphragm D is a coded aperture separate from the coded aperture (OC) of the diaphragm DOC, the image of the object being reconstituted from information acquired at the outlet of the two diaphragms.

In all cases, the apertures (O) and (OC) are equally transparent or opaque to other wavelengths ($\lambda qc$), given that the latter are separate from the work wavelengths ($\lambda w$) and wavelengths ($\lambda d$) for determining the distance.

As a variant, the optical assembly comprises a beam splitter sending back to two separate imagers an image of the object in different frequency bands, one being one or more work frequency band(s) used for acquisition of the image carrying the searched biometric information, the other being one or more other frequency band(s), a centred diaphragm being arranged in front of the imager receiving the image in the work frequency band, the diaphragm with coded aperture being arranged in front of the other imager.

PRESENTATION OF FIGURES

Figure 2:
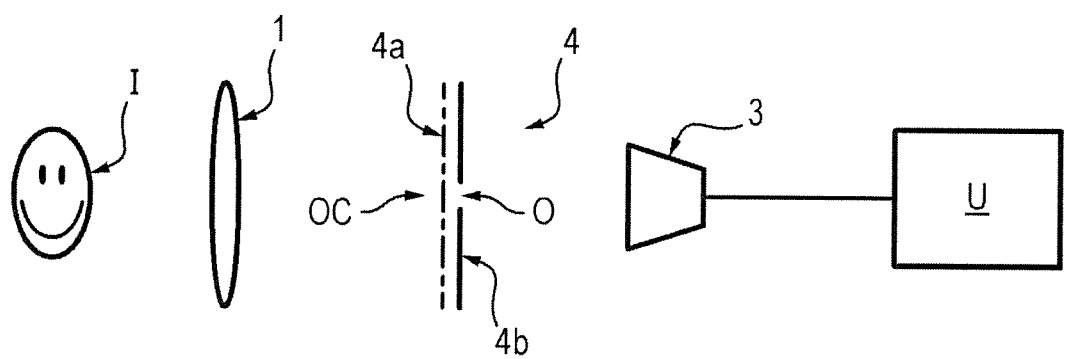

Other characteristics and advantages of the invention will emerge from the following description, which is purely illustrative and non-limiting, and must be considered in conjunction with the appended figures, in which:

FIG. 1 schematically illustrates an acquisition system according to a possible embodiment for the invention;

FIG. 2 illustrates an acquisition system according to another equally possible embodiment.

DESCRIPTION OF ONE OR MORE EMBODIMENTS

In the example illustrated in FIG. 1, the device is intended to acquire an image of the face or iris of the eye of an individual (object I) passing in front of said device.

Of course, it would be used in the same way as for other biometric applications needing "OTF" acquisitions (acquisition "on the fly" images of veins and or fingerprints, for example).

The device comprises an optic 1 and a beam splitter 2 and two imagers or cameras 3a, 3b oriented at 90° one relative to the other and to which the images separated by the beam splitter 2 are sent back.

The camera 3a is linked to a diaphragm 4a with coded aperture interposed between said camera and the beam splitter 2, while the camera 3b is linked to a classic centred and circular diaphragm 4b, interposed between said camera 3b and the beam splitter 2.

The beam splitter 2 is for example a beam splitter which filters colours by transmitting images in different frequency bands to camera 3a and camera 3b.

The images transmitted to camera 3b with classic diaphragm 4b are images in a work frequency band for the relevant biometry, that is, a frequency band which enables exploitation of images acquired to deduce therefrom the searched biometric information.

In the case of acquisition of images of veins or images of irises, it is common to work in the near infrared. The work frequency band filtered by the beam splitter 2 and transmitted to the camera 3b will therefore be selected to be between [700 and 950 nm–]. In the case of acquisition of fingerprint images by contrast, it is common to work on images in the blue-to-green field. For this type of biometry, the work frequency band filtered by the beam splitter 2 and transmitted to the camera 3b will therefore be selected to be between [450 to 650 nm].

The images sent back to the camera 3a with coded aperture diaphragm are as such images in another frequency band and in particular in a frequency band which is not useful for obtaining biometric information.

So for example, this frequency band can be in the IR and be between [800 to 950 nm–].

The image now received by the camera 3a with coded aperture is processed to determine the distance from which the object (the individual I) is situated.

The camera 3b as such receives a fully exploitable image (no information loss) for biometric analysis.

Processing of the images is carried out for example by a single processing unit U to which the different images leaving the cameras 3a, 3b are transmitted.

As a variant, and as illustrated in FIG. 2, the acquisition system can comprise just a single multi-spectral camera 3. One or more diaphragms 4 are interposed between the optic 1 and the camera 3.

This solution has the advantage of costing less than the solution of FIG. 1.

In particular, in a possible embodiment the optical assembly comprises both a standard diaphragm filter 4b for some colours corresponding to at least one work frequency band for the relevant biometry and a diaphragm filter 4a with coded aperture for other colours for determining the distance.

The resulting different images are separated out between the different colours channels of the camera 3 and analysed by the unit U which:

determines the distance from the object I by way of the images in the colours corresponding to the filter 4a;

determines the biometric information on the images in the colours of the filter 4b, by using if needed the information on the distance from the object obtained via the images of the filter 4a.

The filters 4a and 4b are for example coloured filters (slides) with impressions of diaphragms (diaphragm with coded aperture in the case of the filter 4a; centred and circular diaphragm in the case of the filter 4b, for example).

These two filters 4a and 4b can be made in a stack and be in the form of a single element 4.

In a preferred embodiment, since the work wavelengths $\lambda w$ and wavelengths for determining the distance $\lambda d$ are separate wavelengths, the filter 4b which constitutes the diaphragm used for acquisition of the image carrying the searched biometric information comprises an aperture O transparent at least to the work wavelengths $\lambda w$ and the wavelengths $\lambda d$ for determining the distance.

This aperture O is arranged in a semi-opaque surface which is as such opaque to the work wavelengths $\lambda w$, and transparent to the wavelengths ($\lambda d$) for determining the distance.

The filter 4a which constitutes the diaphragm with coded aperture used for acquisition of information for determining the distance comprises as such a semi-opaque surface which is opaque to the wavelengths $\lambda d$ for determining the distance, and transparent to the work wavelengths ($\lambda w$).

It further comprises a coded aperture OC transparent to the work wavelengths $\lambda w$ and the wavelengths $\lambda d$ for determining the distance.

The aperture O of the diaphragm 4b can be a centred and circular aperture for quality acquisition of the image of the object in the work wavelengths $\lambda w$.

According to another possible alternative embodiment, the aperture O of the diaphragm 4b is a coded aperture separate from the coded aperture OC of the diaphragm 4a, the image of the object being reconstituted from information acquired at output of the two diaphragms constituting the filters 4a, 4b.

In all cases, the apertures O and OC are equally transparent or opaque to the other wavelengths $\lambda qc$ which are used neither for quality of the image nor for determining distance. These lengths $\lambda qc$, which are separate from the work wavelengths λw and the wavelengths λd used to determine the distance, are variously filtered or not by the diaphragms 4a, 4b.

Many types of coded apertures are feasible, of course.

Coded apertures of the type of those proposed in the following article could be used, for example:

Levin et al. "Image and Depth from a Conventional Camera with a Coded Aperture"—ACM transactions on graphics, Vol. 26, no. 3, article 70, July 2007.

Calculation of distance performed by the unit U being of the type as described in said article.

In addition, to also improve precision on distance, it is possible to project onto the object observed an image (sight/lighting) at the wavelength used for the filter with coded aperture, projection being done in the axis of the camera. This image adds frequential information missing in the image used for determination of distance.

It is also possible to create 2 coded apertures by well-selected colour filterings. In this case the following is used, for example:

Zhou Et Nayar "Coded Aperture Pairs for Depth from Defocus", 2009—Extended version: International Journal of Computer Vision, May 2011, Volume 93, Issue 1, pp 53-72.

The invention claimed is:

1. Method for acquiring images for a biometric system, wherein the method comprises steps of
providing an optical assembly which receives an input optical signal of an object,
providing a first optical filter configured to selectively transmit frequencies in a first frequency band and a diaphragm with a first coded aperture which convert the input optical signal into a coded optical signal having frequencies only in the first frequency band,
providing a second optical filter configured to selectively transmit frequencies comprises in a second frequency band different from the first frequency band, wherein the second optical filter filters the input optical signal so as to produce a biometric optical signal having frequencies only in the second frequency band,
acquiring a first image of the object from said biometric optical signal, wherein the first image carries biometric information deducible from the first image, and acquiring a second image of the object from the coded optical signal,
determining a distance between the object and the optical assembly from the second image.

2. Method as claimed in claim 1, wherein the first image shows a face, an iris or a vein, wherein the method comprises carrying out a identification or authentication based on the first image.

3. The method according to claim 1, wherein the first optical filter and the second optical filter are stacked together.

4. The method according to claim 1, further comprising projecting an image in the second frequency band onto the object.

5. The method according to claim 1, wherein the first frequency band is a blue frequency band.

6. The method according to claim 1, wherein the diaphragm with the first coded aperture comprises a first semi-opaque surface opaque to the second frequency band and transparent to the first frequency band, and wherein the first coded aperture is transparent to the first frequency band and to the second frequency band.

7. The method according to claim 1, comprising providing a second diaphragm comprising an aperture transparent at least to the first frequency band and to the second frequency band, and a second semi-opaque surface which is opaque to the first frequency band and transparent to the second frequency band.

8. The method according to claim 7, wherein the aperture of the second diaphragm is a centred and circular aperture enabling acquisition of the first image in the first frequency band.

9. The method according to claim 7, wherein the aperture of the second diaphragm is a second coded aperture separate from the first coded aperture, and wherein the first image is reconstituted from optical signals output by the diaphragm with the first coded aperture diaphragm and by the second diaphragm.

10. The method according to claim 1, further comprising
splitting the input optical signal into a first optical signal in the first frequency band and a second optical signal in the second frequency band,
converting the second optical signal into the coded optical signal using the diaphragm with the first coded aperture,
acquiring the first image from the first optical signal using a first imager,
acquiring the second image from the coded optical signal using a second imager different from the first imager.

* * * * *